(12) United States Patent
Kanazawa

(10) Patent No.: US 7,465,271 B2
(45) Date of Patent: Dec. 16, 2008

(54) CAPSULE ENDOSCOPE

(75) Inventor: Masafumi Kanazawa, Tokyo (JP)

(73) Assignee: Hoya Corporation, Tokyo (JP)

( * ) Notice: Subject to any disclaimer, the term of this patent is extended or adjusted under 35 U.S.C. 154(b) by 388 days.

(21) Appl. No.: 10/929,414

(22) Filed: Aug. 31, 2004

(65) Prior Publication Data
US 2005/0049462 A1 Mar. 3, 2005

(30) Foreign Application Priority Data
Sep. 1, 2003 (JP) ............... 2003-309219

(51) Int. Cl.
*A61B 1/06* (2006.01)
*A61B 1/04* (2006.01)

(52) U.S. Cl. .............. 600/179; 600/160; 600/170; 600/178

(58) Field of Classification Search ......... 600/160, 600/109, 476, 407, 176, 179, 170, 178
See application file for complete search history.

(56) References Cited

U.S. PATENT DOCUMENTS

| | | |
|---|---|---|
| 3,683,389 A | 8/1972 | Hollis |
| 4,090,176 A | 5/1978 | Danna et al. |
| 4,217,045 A | 8/1980 | Ziskind |
| 4,262,632 A | 4/1981 | Hanton et al. |
| 4,278,077 A | 7/1981 | Mizumoto |
| 4,439,197 A | 3/1984 | Honda et al. |
| 4,491,865 A | 1/1985 | Danna et al. |
| 4,646,724 A | 3/1987 | Sato et al. |
| 4,741,327 A | 5/1988 | Yabe |
| 4,951,135 A | 8/1990 | Sasagawa et al. |
| 5,010,412 A | 4/1991 | Garriss |
| 5,166,787 A | 11/1992 | Irion |
| 5,167,626 A | 12/1992 | Casper et al. |
| 5,170,801 A | 12/1992 | Casper et al. |
| 5,187,572 A | 2/1993 | Nakamura et al. |
| 5,217,449 A | 6/1993 | Yuda et al. |
| 5,241,961 A | 9/1993 | Henry |
| 5,253,647 A | 10/1993 | Takahashi et al. |
| 5,267,033 A | 11/1993 | Hoshino |
| 5,273,025 A | 12/1993 | Sakiyama et al. |

(Continued)

FOREIGN PATENT DOCUMENTS

DE 2606069 9/1975

(Continued)

OTHER PUBLICATIONS

*Diagnostic Imaging in 3 Easy Steps*, date unknown.

(Continued)

*Primary Examiner*—John P Leubecker
(74) *Attorney, Agent, or Firm*—Greenblum & Bernstein, P.L.C.

(57) ABSTRACT

A capsule endoscope, including an omnidirectional lateral view optical system allowing observation of all directions as the objective optical system and also being capable of illuminating all the image pickup range satisfactorily, is provided. On a positioning plate inside the capsule, six LEDs are arranged at even angular intervals (60 degrees) with their light emitting surfaces facing a transparent cover of the capsule. The light emitting surface of each LED is placed at a position that is a prescribed distance β inwardly apart from the interior surface of the transparent cover of the capsule.

17 Claims, 6 Drawing Sheets

U.S. PATENT DOCUMENTS

| | | | |
|---|---|---|---|
| 5,279,607 | A | 1/1994 | Schentag et al. |
| 5,415,181 | A | 5/1995 | Hogrefe et al. |
| 5,422,636 | A | 6/1995 | Urbas et al. |
| 5,443,066 | A | 8/1995 | Dumoulin et al. |
| 5,604,531 | A | 2/1997 | Iddan et al. |
| 5,662,587 | A | 9/1997 | Grundfest et al. |
| 6,632,216 | B2 | 10/2003 | Houzego et al. |
| 2002/0109774 | A1* | 8/2002 | Meron et al. ............. 348/74 |
| 2003/0171653 | A1* | 9/2003 | Yokoi et al. ............. 600/160 |
| 2004/0092825 | A1* | 5/2004 | Madar et al. ............. 600/473 |
| 2004/0220478 | A1* | 11/2004 | Wallace et al. ............. 600/476 |
| 2004/0254424 | A1* | 12/2004 | Simkulet et al. ............. 600/176 |
| 2005/0004474 | A1* | 1/2005 | Iddan ............. 600/476 |
| 2006/0004255 | A1* | 1/2006 | Iddan et al. ............. 600/160 |
| 2006/0004257 | A1* | 1/2006 | Gilad et al. ............. 600/160 |

FOREIGN PATENT DOCUMENTS

| | | |
|---|---|---|
| DE | 2929429 | 2/1980 |
| DE | 3440177 | 11/1984 |
| EP | 0248867 | 2/1991 |
| JP | 61-122845 | 6/1986 |
| JP | 62-240038 | 10/1987 |
| JP | 2-36849 | 2/1990 |
| JP | 2-159254 | 6/1990 |
| JP | 3-136636 | 11/1991 |
| JP | 4-109927 | 4/1992 |
| JP | 4-144533 | 5/1992 |
| JP | 4-180736 | 6/1992 |
| JP | 5-7573 | 1/1993 |
| JP | 5-15515 | 1/1993 |
| JP | 6-114037 | 4/1994 |
| JP | 6-142081 | 5/1994 |
| JP | 6-285044 | 10/1994 |
| JP | 7-111985 | 5/1995 |
| JP | 57-45833 | 12/1999 |
| JP | 2000-131737 | 5/2000 |
| JP | 2001-223922 | 8/2001 |
| JP | 2002-31766 | 1/2002 |
| JP | 2002-244236 | 8/2002 |
| SU | 1827167 | 7/1993 |
| WO | 87/03465 | 6/1987 |
| WO | 89/01722 | 2/1989 |
| WO | 92/21307 | 10/1992 |
| WO | 94/5200 | 3/1994 |
| WO | 02/054932 | 7/2002 |

OTHER PUBLICATIONS

*The Heidelburg pH Capsule System Telemetric Fasting Gastric Analysis*, date unknown.

Fritscher-Ravens et al., *The Wireless Capsule: New Light in the Darkness*, Digestive Disease, vol. 20, No. 2, 2002.

*Bio-Medical Telemetry: Sensing and transmitting Biological Information from Animals and Man*, R. Stuart Mackay, John Wiley and Sons, New York, 1970, pp. 244-245.

Evan et al., *Studies of the Human Gastro-Intestinal Tract in the Ambulatory Subject Using the Pressure Sensitive Radiotelemetry Capsule*.

Lange et al., *Heidelberger Kapsel—ein Kleinstesender fur die pH-Messung im Magen*, Telefunk-Zeitung, vol. 36, No. 5, 1963, pp. 265-270.

Manual of Photogrammetry, vol. 1, Third Edition, American Society of Photogrammetry, 1966, pp. 812-813.

P. Swain, *Wireless Capsule Endoscopy*, Gut, vol. 52 (Suppl. IV), 2003, iv48-iv50.

Rowlands et al., *The Radio Pill: Telemetering from the Digestive Tract*, British Communications and Electronics, Aug. 1960, pp. 598-601.

Leung et al., *Wireless Capsule Endoscopy in Chinese Patients with Suspected Small Bowel Diseases*, Hong Kong Med J. vol. 10, 2004, pp. 179-183.

Yarbrough III et al., *Evaluation of the Heidelberg pH Capsule: Method of Tubeless Gastric Analysis*, The American Journal of Surgery, vol. 117, Feb. 1969, pp. 185-192.

English language Abstract of German 3440177.
English language Abstract of JP 2-159254.
English language Abstract of JP 4-144533.
English language Abstract of JP 3-136636.
English language Abstract of JP 5-15515.
English language Abstract of JP 5-7573.

* cited by examiner

CAPSULE ENDOSCOPE

BACKGROUND OF THE INVENTION

The present invention relates to a capsule endoscope which is introduced into a body cavity of a patient for picking up images of the inside of the body cavity.

In recent years, a capsule endoscope system, including a capsule endoscope (an endoscope in the shape of a small capsule) which is swallowed by a patient to be introduced into the patient's body cavity for picking up images of the inside of the body cavity and a processor and a monitor which are placed outside the patient's body, is being developed in order to eliminate the pain of patients in orally introducing (swallowing) the tip of a conventional electronic endoscope formed as a flexible tube.

The capsule endoscope swallowed (orally introduced into a body cavity) by the patient picks up an image of the inside of the body cavity, converts the image into an image signal, and wirelessly transmits the image signal to the processor placed outside the patient's body. The processor receives and processes the image signal and thereby displays the image of the inside of the body cavity on the monitor. Since such a capsule endoscope only requires patients to swallow a small capsule, observation of the inside of the alimentary canal, etc. can be carried out without causing pain to the patients.

FIG. 9 is a schematic diagram showing a capsule endoscope which is employed for a capsule endoscope system. As shown in FIG. 9, the capsule endoscope 100 is enclosed and sealed up by a casing in the shape of a capsule. The capsule endoscope 100 is mainly composed of an objective optical system 101, an image sensor 102 for picking up an image of the inside of a body cavity through the objective optical system 101 and converting the image into an image signal, a signal processing circuit 103 for processing the image signal outputted by the image sensor 102, a transmitter 104 for transmitting the image signal processed by the signal processing circuit 103 to a processor which is placed outside the patient's body, a battery 105 for supplying electromotive force to each component of the capsule endoscope 100, and a lighting unit 106 for illuminating the inside of the body cavity (image pickup range).

The capsule endoscope 100 swallowed (introduced into the body cavity) by the patient is powered by the battery 105. By the capsule endoscope 100, an image of the inside of the body cavity is captured by the image sensor 102, an image signal representing the image is obtained by the signal processing circuit 103, and the image signal is transmitted to the processor by the transmitter 104.

However, with such a capsule endoscope 100 being introduced into a body cavity, it is very difficult to control the direction of the objective optical system 101 (that is, to control the attitude of the capsule endoscope 100). Even if the attitude control of the capsule endoscope 100 is made possible, in order to capture an image of an organ having a large interior wall area (stomach, etc.) by use of the capsule endoscope 100, the image pickup range of the capsule endoscope 100 has to be shifted bit by bit by changing its attitude while capturing a plurality of images and that takes a very long time. Therefore, employment of an objective optical system having a wider field of view as the objective optical system 101 of the capsule endoscope 100 is being hoped for in order to realize more efficient observation.

As an objective optical system having a wide field of view, there exists the so-called omnidirectional image pickup optical system (omnidirectional lateral view optical system) having a field of view of 360 degrees (omnidirectional) around the optical axis of the object lens and being mainly employed as the objective optical system of a monitoring camera (see Japanese Patent Provisional Publication No.2000-131737, for example). FIG. 10 is a schematic diagram showing an example of the application of such an omnidirectional lateral view optical system to an objective optical system of a capsule endoscope. The omnidirectional lateral view optical system includes an object lens 201 and a convex reflecting mirror 210 in the shape of a paraboloid of revolution which is placed in front of the object lens 201, by which an omnidirectional image can be formed on an image pickup plane through the object lens 201. As shown in FIG. 10, the convex reflecting mirror 210 is placed so that its central axis will be coaxial with the optical axis of the object lens 201. Object light (light reflected by the object) within an image pickup range a is reflected by the convex reflecting mirror 210 toward the object lens 201 and is focused on the image pickup plane of an image pickup sensor (photoreceptor) 202 by the object lens 201.

By employing such an omnidirectional image pickup optical system as the objective optical system of a capsule endoscope, an image pickup device having a wide field of view can be realized, by which a wide range inside a body cavity can be observed efficiently regardless of the attitude of the capsule endoscope.

However, even though the aforementioned omnidirectional lateral view optical system is originally designed to be applicable to indoor shooting, capturing images inside a body cavity (with almost no light reaching the object in comparison with indoor shooting with a certain amount of light) by use of such an omnidirectional lateral view optical system is almost impossible. Even if a lighting unit employed for image pickup devices in conventional endoscopes (illumination by an optical fiber, an LED, etc.) is applied to a capsule endoscope having the omnidirectional lateral view optical system, resultant observable range is limited to a narrow range due to the difference between the illumination range of the lighting unit (optical axis direction of the object lens 201) and the image pickup range of the omnidirectional lateral view optical system (all directions orthogonal to the optical axis of the object lens 201).

SUMMARY OF THE INVENTION

The present invention is advantageous in that it provides a capsule endoscope configured to have an omnidirectional lateral view optical system allowing observation of all directions as an objective optical system and to be capable of illuminating all the image pickup range satisfactorily.

In accordance with an aspect of the present invention, there is provided a capsule endoscope, which includes a capsule in a substantially cylindrical shape with closed ends. The capsule has a transparent part which is formed at at least one axial position of the capsule to be transparent around all the circumference of the capsule.

The capsule endoscope further includes an omnidirectional objective optical system which is placed to be substantially coaxial with a central axis of the capsule to receive light reflected by objects existing around all the circumference of the capsule through the transparent part and focuses an image of the objects on a single image plane which is substantially orthogonal to the central axis of the capsule, an image pickup device which picks up the image focused by the omnidirectional objective optical system and converts the image into an image signal, and a plurality of light emitting elements arranged at even angular intervals inside the transparent part of the capsule for illuminating substantially all of the image pickup range shot by the omnidirectional objective optical system and the image pickup device.

Further, the capsule endoscope includes a transmitter which wirelessly transmits the image signal outputted by the image pickup device to the outside of the capsule, and an electric power supply which supplies driving currents to the image pickup device, the light emitting elements and the transmitter.

In the above configuration of the capsule endoscope, the plurality of light emitting elements are arranged at even angular intervals inside the transparent part of the capsule, by which a peripheral part of an area illuminated by a light emitting element (where light quantity is low) overlaps with a peripheral part of an adjacent area illuminated by an adjacent light emitting element and thereby all the image pickup range (in all directions orthogonal to the optical axis of the objective optical system) can be illuminated evenly and satisfactorily.

Optionally, each of the plurality of light emitting elements may be placed so that a central axis of the illuminating light emitted therefrom will be orthogonal to the optical axis of the omnidirectional objective optical system.

By such arrangement of the light emitting elements, illuminating areas of adjacent light emitting elements overlap with each other regularly and thereby all the image pickup range can be illuminated evenly and excellently.

Alternatively, each of the plurality of light emitting elements may also be placed so that a central axis of the illuminating light emitted therefrom is in a tangential direction of a virtual circle which is assumed to be coaxial with the omnidirectional objective optical system.

By such arrangement of the light emitting elements, the optical path length from each light emitting element to the transparent part of the capsule can be made longer than that in the case where the central axis of the illuminating light is set orthogonal to the optical axis of the omnidirectional objective optical system, by which the illuminating area of each light emitting element can be made wider. Further, the number of light emitting elements that can be arranged can be increased compared to the case where the central axis of the illuminating light is set orthogonal to the optical axis of the omnidirectional objective optical system. Therefore, illuminating areas of adjacent light emitting elements overlap with each other from the vicinity of the capsule and thereby all the image pickup range can be illuminated more excellently.

Still optionally, the plurality of light emitting elements may be alternately arranged around the optical axis of the omnidirectional objective optical system at first radial positions nearer to the optical axis and second radial positions farther from the optical axis.

By such arrangement of the light emitting elements, the optical path length from each light emitting element at the first radial position to the transparent part of the capsule can be made longer and thereby the illuminating area of each light emitting element at the first radial position can be made wider. Therefore, illuminating areas of adjacent light emitting elements overlap with each other from the vicinity of the capsule and thereby all the image pickup range can be illuminated excellently.

In a particular case, the plurality light emitting elements may be lateral light-emission diodes.

Still optionally, the plurality of light emitting elements may be placed at positions avoiding interference with object light passing through the transparent part of the capsule and focusing on the image plane via the omnidirectional objective optical system.

By such arrangement of the light emitting elements, the object light (light reflected by the object (body cavity wall)) can be prevented from being blocked or deflected by the light emitting elements.

Still optionally, the plurality of light emitting elements may be placed on both sides of object light passing through the transparent part of the capsule and incident upon the omnidirectional objective optical system to focus on the image plane.

By such arrangement of the light emitting elements, each part in the image pickup range can be illuminated by two light emitting elements apart from each other in the optical axis direction of the omnidirectional objective optical system, by which shadows in the image pickup range (due to concavities and convexities of the body cavity wall) can be prevented.

In a particular case, the light emitting elements may include six light emitting elements being arranged at even angular intervals of 60 degrees inside the transparent part of the capsule. However, detailed specifications like the number of light emitting elements arranged inside the transparent part can of course be changed according to design requirements, etc.

Still optionally, the omnidirectional objective optical system may include an object lens group which focuses the image of the objects on the image plane, and a convex reflecting mirror which reflects object light entering the capsule through the transparent part and thereby guides the object light to the object lens group.

Still optionally, the convex reflecting mirror may be formed in the shape of a paraboloid of revolution and placed to be coaxial with the optical axis of the object lens group.

According to another aspect of the invention, there is provided a capsule endoscope, which is provided with a capsule configured to have hermeticity and to have a transparent part to transmit light, an objective optical system which is placed to be substantially coaxial with a predetermined axis defined in the capsule to receive light reflected by objects and focuses an image of the objects on a single image plane which is substantially orthogonal to the predetermined axis of the capsule, and an image pickup device which picks up the image focused by the objective optical system and converts the image into an image signal. The capsule endoscope is further provided with a plurality of light emitting elements arranged at even angular intervals inside the capsule for illuminating substantially all of the image pickup range shot by the objective optical system and the image pickup device, a transmitter which wirelessly transmits the image signal outputted by the image pickup device, and an electric power supply which supplies driving currents to the image pickup device, the plurality of light emitting elements and the transmitter.

With this configuration, all the image pickup range can be illuminated sufficiently.

According to another aspect of the invention, there is provided a capsule endoscope, which is provided with a capsule configured to have hermeticity and to have a transparent part which is formed at at least one axial position of a predetermined axis defined in the capsule to be transparent around all the circumference of the capsule, and an omnidirectional objective optical system which is placed to be substantially coaxial with the predetermined axis of the capsule to receive light reflected by objects existing around all the circumference of the capsule through the transparent part and focuses an image of the objects on a single image plane which is substantially orthogonal to the predetermined axis of the capsule. The capsule endoscope is further provided with an image pickup device which picks up the image focused by the omnidirectional objective optical system and converts the image into an image signal, a plurality of light emitting elements arranged at even angular intervals inside the transparent part of the capsule for illuminating substantially all of the image pickup range shot by the omnidirectional objective optical system and the image pickup device, a transmitter which wirelessly transmits the image signal outputted by the image pickup device, and an electric power supply which supplies driving currents to the image pickup device, the plurality of light emitting elements and the transmitter.

With this configuration, all the image pickup range can be illuminated sufficiently.

BRIEF DESCRIPTION OF THE ACCOMPANYING DRAWINGS

The objects and features of the present invention will become more apparent from the consideration of the following detailed description taken in conjunction with the accompanying drawings, in which.

DETAILED DESCRIPTION OF THE EMBODIMENTS

Figure 1:
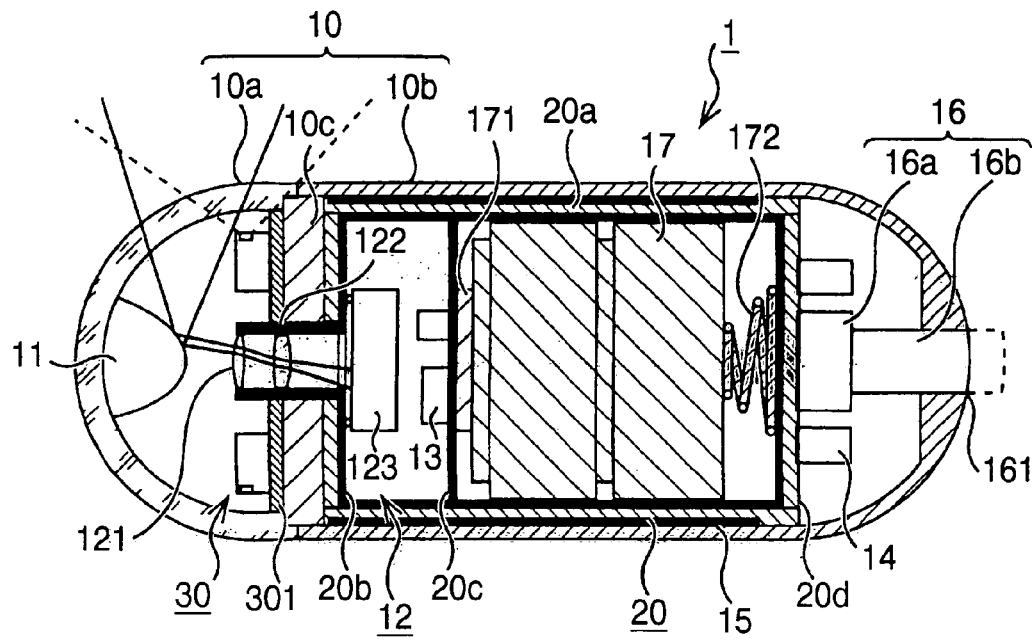
FIG. 1 is a schematic diagram showing the internal composition of a capsule endoscope in accordance with a first embodiment of the present invention.

Referring now to the drawings, a description will be given in detail of preferred embodiments in accordance with the present invention. Each capsule endoscope provided by the present invention is an endoscope in the shape of a capsule which is orally introduced into a body cavity by a patient (subject) and picks up images inside the body cavity while transmitting image signals (representing the images of the inside of the body cavity) to an unshown processor which is placed outside the patient's body.

First Embodiment

FIG. 1 is a schematic diagram showing the internal composition of a capsule endoscope 1 in accordance with a first embodiment of the present invention. For the sake of clear and easy understanding of the explanation, part of the capsule endoscope 1 drawn on the left-hand side of FIG. 1 will be called "the front" and part of the capsule endoscope 1 drawn on the right-hand side of FIG. 1 will be called "the rear".

As shown in FIG. 1, the capsule endoscope 1 includes a convex reflecting mirror 11, an image pickup device 12, an image processing circuit 13, a transmission circuit 14, a transmission antenna 15, a lighting unit 30, a battery 17 supplying electric power to each component, an internal case 20 storing the battery 17 and electrically connecting circuit components (explained later) mounted thereon, a power switch 16, and a casing 10 storing and protecting the above components.

The casing 10 includes a cylindrical body 10b having a hemispheric rear end, a transparent cover 10a which is attached to the front end of the body 10b to project in a hemispheric shape, and a reinforcing member 10c which is fixed inside the body 10b. Thus, the casing 10 is formed in the so-called capsule shape as a whole. The transparent cover 10a, made of resin which is transparent and resistant to acids, has a function of maintaining a proper distance between the image pickup device 12 and the object (body cavity wall). On the central axis of the body 10b, a switch hole 161 is formed for letting the power switch 16 protrude therefrom. The body 10b is formed of resin which is light shielding and acid resistant. The reinforcing member 10c, having a cylindrical shape with a radius slightly smaller than that of the body 10b, is fixed inside the body 10b so that its front surface will be slightly in front of the front edge of the body 10b. On the central axis of the reinforcing member 10c, a hole is formed for letting the body tube 122 of the image pickup device 12 (described later) protrude therefrom.

The convex reflecting mirror 11 is a reflecting mirror in the shape of a paraboloid of revolution, for reflecting and deflecting illuminating light reflected by the body cavity wall (hereinafter, referred to as "reflected light from the body cavity wall" or "object light") and thereby guiding the reflected light to an object lens group 121 of the image pickup device 12 which will be described later. The convex reflecting mirror 11 is fixed to the interior wall of the transparent cover 10a so that the central axis of the paraboloid of revolution will be coaxial with the central axis of the hemispheric transparent cover 10a and its apex will project toward the rear (inside of the hemispheric transparent cover 10a).

The image pickup device 12 includes the object lens group 121 stored in the body tube 122 and an image sensor 123. The image pickup device 12 captures images of the body cavity wall by letting the object lens group 121 focus the reflected light from the body cavity wall reflected by the convex reflecting mirror 11 on the image sensor 123. The image sensor 123 is installed with its center placed at the position where the image of the body cavity wall is focused by the object lens group 121. The image pickup device 12 is fixed so that the optical axis of the object lens group 121 stored inside the body tube 122 will be coaxial with the central axis of the convex reflecting mirror 11, by letting the body tube 122 penetrate the holes formed in the reinforcing member 10c, a positioning plate 301 and a front end circular plate 20b.

The lighting unit 30, including six LEDs (Light Emitting Diodes) 30a-30f and the positioning plate 301 on which the LEDs 30a-30f are fixed, emits illuminating light (white light) toward the object (body cavity wall). In the following, the specific composition of the lighting unit 30 will be explained in detail referring to FIGS. 2 through 4.

Figure 2:
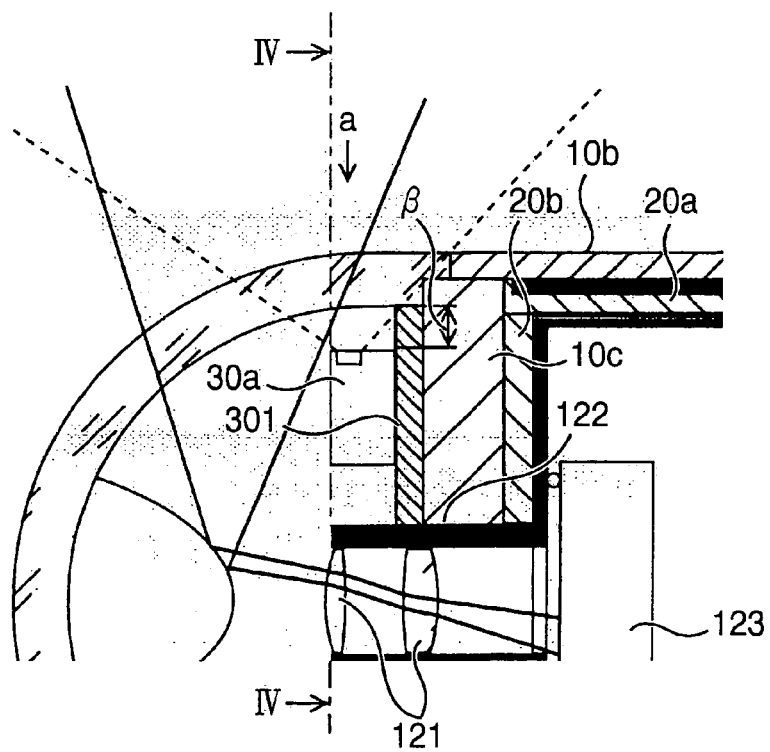
FIG. 2 is a schematic diagram enlarging part of the capsule endoscope around an LED of a lighting unit.
Figures 3A, 3B:
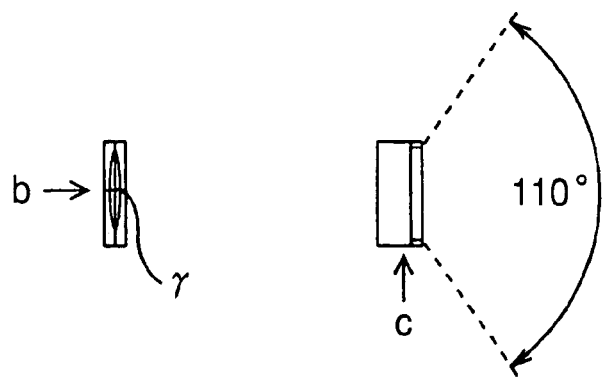
FIG. 3A through 3C are schematic diagrams showing the LED seen in three directions.
Figure 3C:
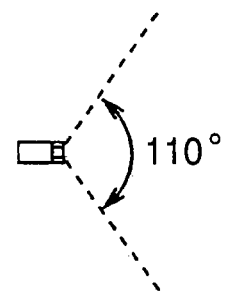
Figure 4:
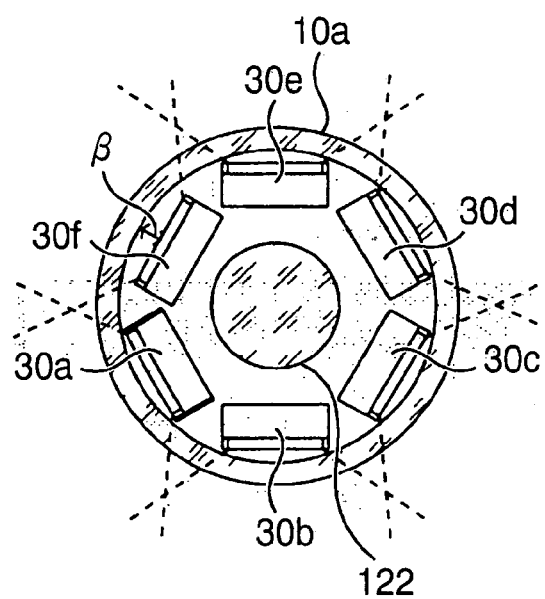
FIG. 4 is a cross-sectional view showing a cross section along a chain line IV shown in FIG. 2.

FIG. 2 is a schematic diagram enlarging part of the capsule endoscope 1 around an LED 30a of the lighting unit 30. FIG. 3A through 3C are schematic diagrams showing the LED 30a seen in three directions, in which FIG. 3A views the LED 30a in the direction "a" shown in FIG. 2, FIG. 3B views the LED 30a in the direction "b" shown in FIG. 3A, and FIG. 3C views the LED 30*a* in the direction "c" shown in FIG. 3B, respectively. FIG. 4 is a cross-sectional view showing a cross section along the chain line IV shown in FIG. 2.

As shown in FIG. 3, each LED 30*a*-30*f* is the so-called lateral diode (lateral light-emission diode) in the shape of a thin rectangular prism, emitting diverging light (shown with broken lines in each figure) as the illuminating light from its lateral face shown in FIG. 3A. The illuminating light (diverging light) emitted by each LED 30*a*-30*f* diverges at an angle of approximately 110 degrees. As the lateral diode, "surface-mounted LEDs" NSCW215, NSCW335, NSCW505, etc. (Nichia Corporation), "white chip LEDs" GM4VG31320AC (Sharp Corporation), etc. can be used suitably.

As shown in FIGS. 2 and 4, the positioning plate 301 is a circular plate having a center hole of a size just enough for letting the body tube 122 of the image pickup device 12 protrude therefrom. The positioning plate 301 has an under surface of an external diameter approximately the same as the internal diameter of the transparent cover 10*a* and is fixed on the front surface of the reinforcing member 10*c* to be coaxial with the body 10*b*. On the positioning plate 301, the aforementioned six LEDs 30*a*-30*f* are arranged at fixed positions around the image pickup device 12 at even angular intervals (60 degrees) with their light emitting surfaces (the aforementioned lateral faces) facing the transparent cover 10*a* (facing the direction opposite to the image pickup device 12). It should be noted that the angular interval of 60° is obtained by dividing 360° by six (i.e., the number of LEDs 30*a*-30*f*). Incidentally, the direction of the central axis of each illuminating light emitted from each LED 30*a*-30*f* is orthogonal to the optical axis of the object lens group 121 of the image pickup device 12.

In order to prevent the development of a dead zone (where the illuminating light from the lighting unit 30 can not reach) outside the transparent cover 10*a*, the center γ of the light emitting surface of each LED 30*a*-30*f* (hereinafter the position of the center γ of the light emitting surface will be regarded as a "reference position" indicating the position of each LED) is placed at a position that is a prescribed distance β apart from the interior surface of the transparent cover 10*a* toward the image pickup device 12 (body tube 122) (see FIGS. 2 and 4). The inward placement of the LEDs 30*a*-30*f* from the transparent cover 10*a* by the distance β also serves for preventing the object light (light from the object) incident upon the convex reflecting mirror 11 from being blocked or deflected by the LEDs 30*a*-30*f*.

The internal case 20 includes a lateral plate 20*a* in a cylindrical shape, a front end circular plate 20*b* in a disk-like shape, an internal circular plate 20*c* (disk-like shape) and a rear end circular plate 20*d* (disk-like shape). The circular plates 20*b*-20*d* are accommodated in the lateral plate 20*a* to be coaxial with the lateral plate 20*a* and in parallel with one another. The front end circular plate 20*b* and the rear end circular plate 20*d* are fixed to the front end and rear end of the lateral plate 20*a*, respectively. The internal circular plate 20*c* is fixed inside the lateral plate 20*a* at a position approximately ¼ of the length of the lateral plate 20*a* from the front end.

Various components are mounted on the plates 20*a*-20*d* forming the internal case 20. Specifically, the transmission antenna 15 is printed on the whole external surface of the lateral plate 20*a*. As mentioned above, a hole for letting the body tube 122 of the image pickup device 12 protrude therefrom is formed on the central axis of the front end circular plate 20*b*, and the front surface of the front end circular plate 20*b* is bonded to the reinforcing member 10*c*. On the rear surface of the front end circular plate 20*b*, the image sensor 123 of the image pickup device 12 is mounted. The image processing circuit 13 is mounted on the front surface of the internal circular plate 20*c*, while an anode contact part 171 as a circuit component contacting the anode of the battery 17 is mounted on the rear surface of the internal circular plate 20*c*. A spring-like cathode contact part 172 as a circuit component contacting the cathode of the battery 17 is mounted on the front surface of the rear end circular plate 20*d*. The transmission circuit 14 and the power switch 16 are mounted on the rear surface of the rear end circular plate 20*d*.

Between the internal circular plate 20*c* and the rear end circular plate 20*d*, the battery 17 as a primary cell is stored. Circuit patterns for electrically connecting the above circuit components are also printed on the plates 20*a*-20*d* forming the internal case 20. The circuit patterns on the circular plates 20*b*-20*d* are electrically connected to the circuit pattern on the lateral plate 20*a* via unshown wires. When the power is ON, driving current is supplied from the battery 17 to each circuit component via the circuit patterns. Unshown wires are connected to the circuit pattern on the front end circular plate 20*b*, by which the LEDs 30*a*-30*f* of the lighting unit 30 are electrically connected to the front end circular plate 20*b*.

The image processing circuit 13 is a circuit for receiving the image signal representing an image of the body cavity wall captured by the image pickup device 12, processing the image signal (noise reduction, etc.), and sending the processed image signal to the transmission circuit 14. The transmission circuit 14 generates a transmission signal by processing (modulation, amplification, etc.) the image signal supplied from the image processing circuit 13 and sends the transmission signal to the transmission antenna 15. The transmission antenna 15 is an antenna for wirelessly transmitting the transmission signal to the unshown processor which is placed outside the body of the patient (subject).

The power switch 16 includes a switch mechanism 16*a* and a cylindrical projection 16*b* having a radius slightly smaller than that of the switch hole 161. The power switch 16 is attached on the rear surface of the rear end circular plate 20*d* so that its central axis will be coaxial with the central axis of the rear end circular plate 20*d*. The negative wire of the switch mechanism 16*a* is electrically connected to the cathode contact part 172 on the rear end circular plate 20*d*, while the positive wire of the switch mechanism 16*a* is electrically connected to the circuit pattern on the rear end circular plate 20*d*. The packages of the switch mechanism 16*a* and the projection 16*b* are formed of an insulator. The interface between the switch hole 161 and the projection 16*b* is sealed with an unshown sealing material to make the interface watertight.

When the power of the capsule endoscope 1 is OFF, the circuit inside the switch mechanism 16*a* is open and no driving current passes inside the capsule endoscope 1. In this state, the projection 16*b* of the power switch 16 protrudes rearward from the switch hole 161 of the body 10*b* (as shown with the broken line in FIG. 1). By pressing the projection 16*b* frontward, the circuit inside the switch mechanism 16*a* closes and thereby driving current is supplied from the battery 17 to each circuit component of the capsule endoscope 1 via the aforementioned circuit patterns and wires (i.e., power is turned ON).

When the power switch 16 is pressed and each circuit component of the capsule endoscope 1 is activated, each LED 30*a*-30*f* of the lighting unit 30 emits the illuminating light. The capsule endoscope 1 turned ON is swallowed by the patient and thereby introduced into a body cavity of the patient. The illuminating light is applied to the body cavity wall of the patient through the transparent cover 10*a*, and the reflected light from the body cavity wall is deflected by the convex reflecting mirror 11, incident upon the object lens group 121 of the image pickup device 12, and focused on the image sensor 123. The image of the patient's body cavity wall is picked up (converted into an image signal) by the image sensor 123 and sent to the image processing circuit 13. The image processing circuit 13 executes a prescribed process to the input image signal and outputs the processed image signal to the transmission circuit 14. The image signal is converted by the transmission circuit 14 into the transmission signal by modulation and amplification, and the transmission signal is outputted to the transmission antenna 15. The transmission signal is wirelessly transmitted by the transmission antenna 15 to the unshown processor placed outside the body. The processor is a device for generating a video signal (that can be processed and displayed by a monitor) by executing prescribed image processing to the transmission signal received from the transmission antenna 15. The processor which received the transmission signal generates the video signal based on the transmission signal and lets the monitor display an image by the video signal.

As described above, in the capsule endoscope 1 in accordance with the first embodiment of the present invention, the six LEDs 30a-30f of the lighting unit 30 are placed at proper positions that can let illuminating areas of the LEDs 30a-30f overlap with one another outside the transparent cover 10a and prevent the object light (reflected light from the body cavity wall) from being blocked or deflected by the LEDs 30a-30f. Therefore, by use of the capsule endoscope 1 having the lighting unit 30 composed as above, all the field of view in all directions around the capsule endoscope 1 can be illuminated and shot effectively and efficiently.

Second Embodiment

Figure 5:
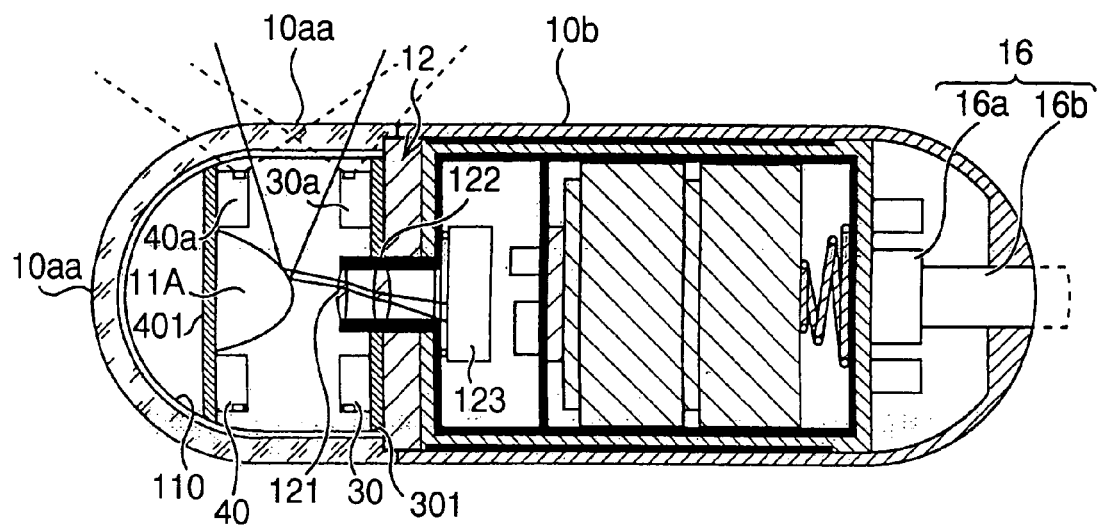
FIG. 5 is a schematic diagram showing the internal composition of a capsule endoscope in accordance with a second embodiment of the present invention.
Figure 6:
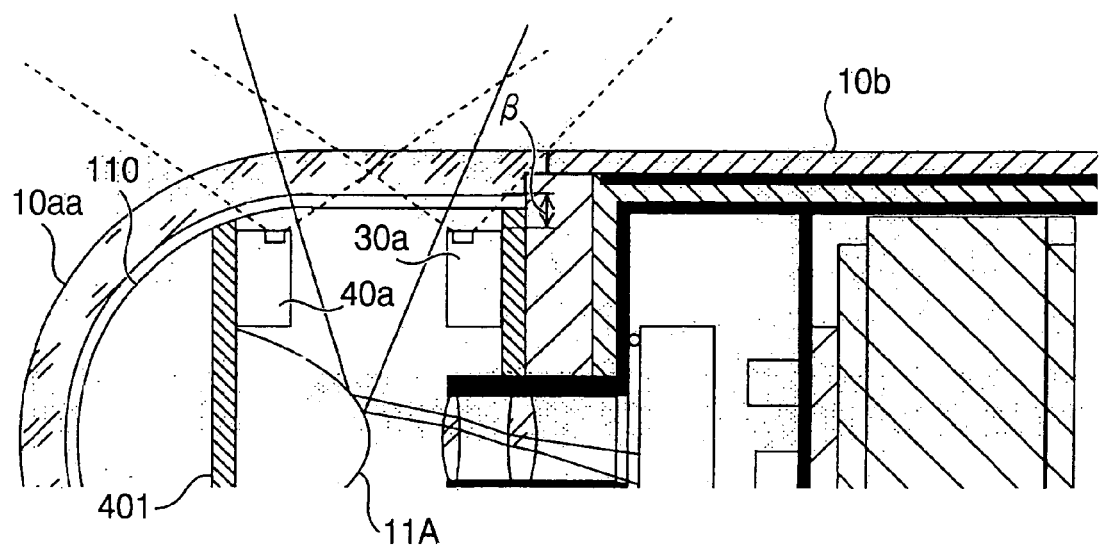
FIG. 6 is a schematic diagram enlarging part of the capsule endoscope around two LEDs of a lighting unit.

FIG. 5 is a schematic diagram showing the internal composition of a capsule endoscope 1B in accordance with a second embodiment of the present invention. FIG. 6 is a schematic diagram enlarging part of the capsule endoscope 1B around two LEDs 30a and 40a of the lighting unit 30. In FIGS. 5 and 6, the same reference numerals as those of the first embodiment designate the same components as those of the first embodiment and thus repeated description thereof is omitted for brevity.

A transparent cover 10aa is formed of a transparent and acid resistant material in a substantially cylindrical shape to have a hemispheric front end. The internal surface of the transparent cover 10aa is coated with a transparent electrically conductive material (transparent conductive layer 110) such as ITO (Indium Tin Oxide). The transparent conductive layer 110 is formed into a circuit pattern by photo-lithography, etching, etc., and a positive wire and negative wire of the circuit pattern are electrically connected to the circuit patterns on the internal case 20 by wire bonding, etc.

Inside the transparent cover 10aa, a front positioning plate 401 is fixed at the interface between the cylindrical part and the hemispheric part of the transparent cover 10aa to be coaxial with its central axis. On the rear surface of the front positioning plate 401, a convex reflecting mirror 11A and a front lighting unit 40 are fixed.

The convex reflecting mirror 11A, a reflecting mirror in the shape of a paraboloid of revolution similarly to the convex reflecting mirror 11, is placed coaxially with the central axis of the front positioning plate 401.

The front lighting unit 40, including six LEDs 40a-40f fixed on the front positioning plate 401 similarly to the lighting unit 30, emits illuminating light toward the object. The LEDs 40a-40f are electrically connected to the circuit pattern formed by the transparent conductive layer 110 by wire bonding, etc. The six LEDs 40a-40f are arranged around the convex reflecting mirror 11A at even angular intervals (60 degrees) with their light emitting surfaces facing the transparent cover 10aa, similarly to the LEDs 30a-30f. It should be noted that the angular interval of 60° is obtained by dividing 360° by six (i.e., the number of LEDs 40a-40f). Each LED 40a-40f is placed at a position that is shifted inward (toward the convex reflecting mirror 11A) from the interior surface of the transparent cover 10aa by the distance β, similarly to each LED 30a-30f.

In short, the capsule endoscope 1B of the second embodiment is provided with the front lighting unit 40 in addition to the lighting unit 30. Therefore, areas of the object (body cavity wall) to which the illuminating light from the lighting unit 30 of the capsule endoscope 1 of the first embodiment can not reach can also be covered and illuminated sufficiently by the front lighting unit 40. By the application of the illuminating light to the object from two directions, shadows in the observed area can be prevented.

Further, since the convex reflecting mirror 11A is fixed on the rear surface of the front positioning plate 401, a space can be reserved in front of the front positioning plate 401. The space can also be used for storing other circuit components, medicines, etc.

In the following, two examples of modifications of the arrangement of the LEDs 30a-30f on the positioning plate 301 of the lighting unit 30 and the LEDs 40a-40f on the front positioning plate 401 of the front lighting unit 40 will described in detail. In the following examples, the LEDs 30a-30f on the positioning plate 301 and the LEDs 40a-40f on the front positioning plate 401 are arranged in the same way, and thus only the LED arrangement in the lighting unit 30 will be explained omitting the explanation of the LED arrangement in the front lighting unit 40.

Figure 7:
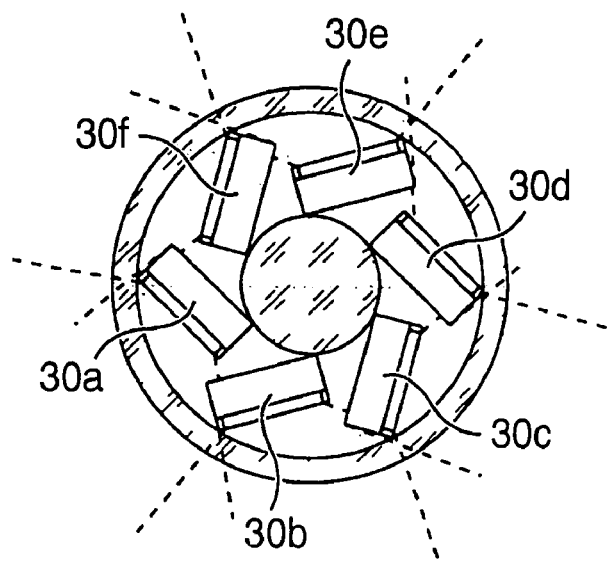
FIG. 7 is a schematic diagram showing a first modification of LED arrangement in the lighting unit.

FIG. 7 is a schematic diagram showing a first modification of the LED arrangement in the lighting unit 30. In the first modification shown in FIG. 7, the LEDs 30a-30f are arranged around the image pickup device 12 (body tube 122) with their light emitting surfaces facing the transparent cover 10a (or 10aa) so that the central axis of the illuminating light emitted by each LED 30a-30f will be in a tangential direction of a virtual circle which is assumed to be coaxial with the object lens group 121 (i.e. the LEDs 30a-30f are arranged like vanes of a windmill). By such arrangement of the LEDs 30a-30f, dead zones can be covered more effectively and the number of LEDs that can be arranged can also be increased, by which the body cavity wall can be illuminated more efficiently.

Figure 8:
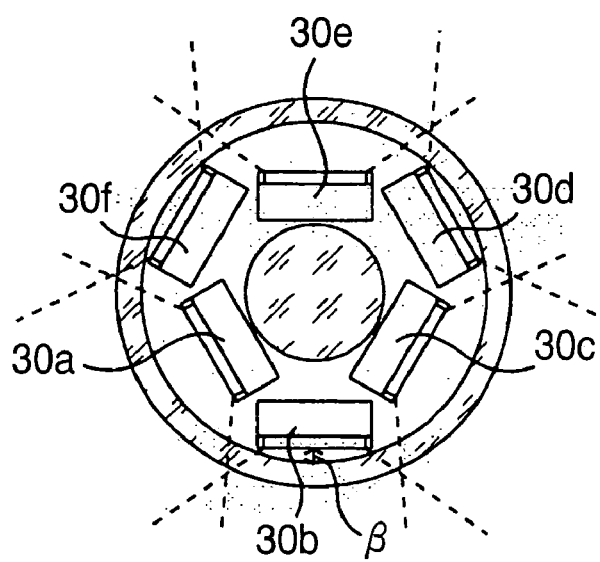
FIG. 8 is a schematic diagram showing a second modification of LED arrangement in the lighting unit.
Figure 9:
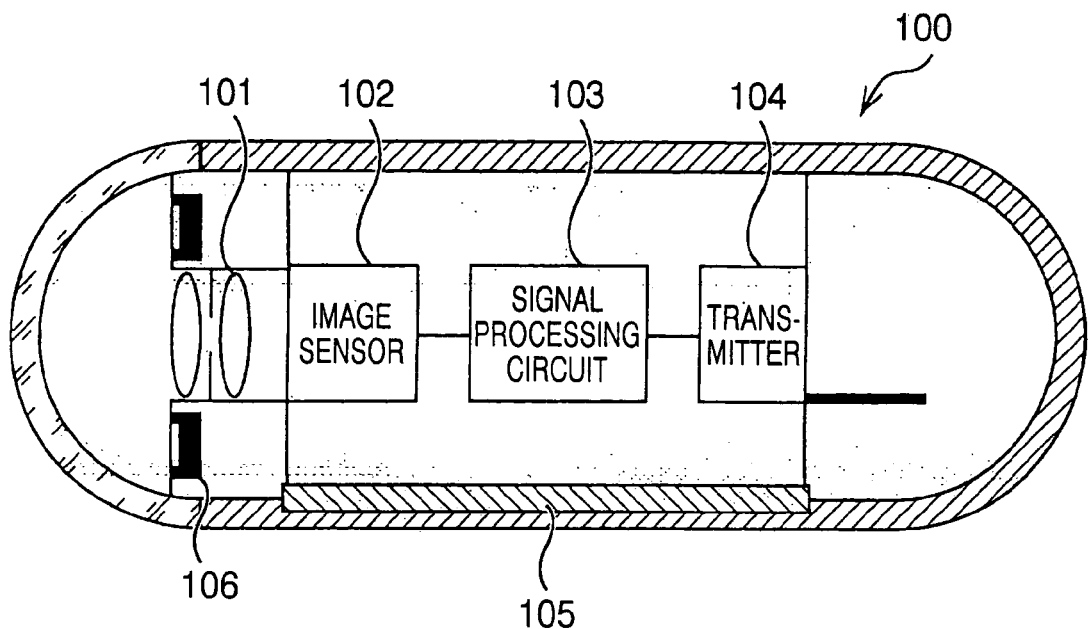
FIG. 9 is a schematic diagram showing a conventional capsule endoscope.
Figure 10:
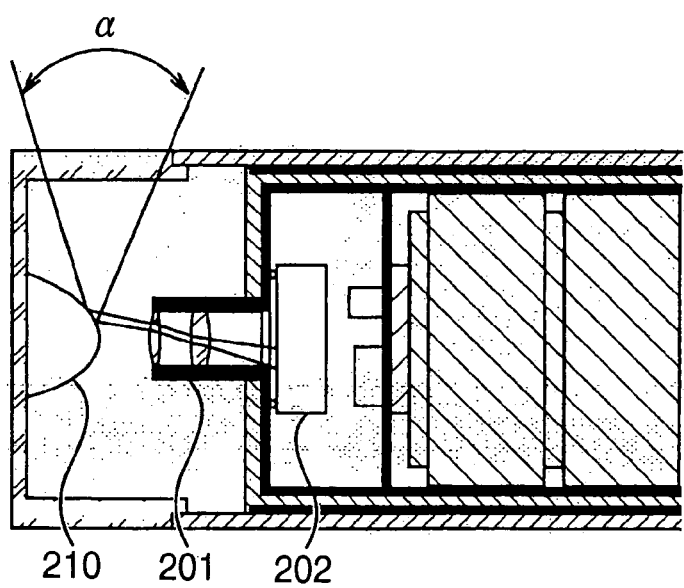
FIG. 10 is a schematic diagram showing an example of the application of an omnidirectional lateral view optical system to an objective optical system of a capsule endoscope.

FIG. 8 is a schematic diagram showing a second modification of the LED arrangement in the lighting unit 30. In the second modification shown in FIG. 8, the LEDs 30a-30f are alternately arranged at two radial positions: inside positions (first radial positions) and outside positions (second radial positions). In this case, the three LEDs 30b, 30d and 30f at the outside positions are a prescribed distance β apart from the internal surface of the transparent cover 10a, while the three LEDs 30a, 30c and 30e at the inside positions are a prescribed distance longer than β apart from the internal surface. Also by such arrangement of the LEDs 30a-30f, the dead zones can be satisfactorily covered by the illuminating light.

While the present invention has been described with reference to the particular illustrative embodiments, it is not to be restricted by those embodiments but only by the appended claims. For example, it is possible to properly combine different arrangements of the LEDs 30a-30f and the LEDs 40a-40f together. It is to be appreciated that those skilled in the art can change or modify the embodiments without departing from the scope and spirit of the present invention.

Figure 11A:
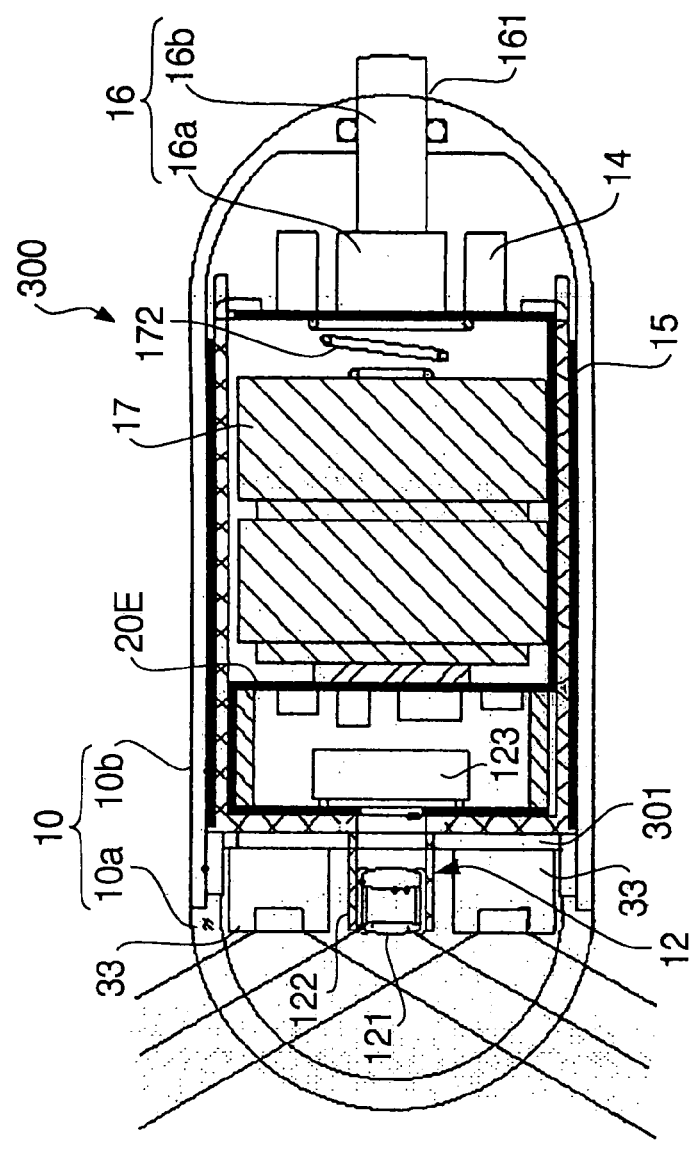
FIG. 11A is a schematic diagram showing an internal configuration of a direct view capsule endoscope.

The above mentioned arrangements of LEDs in the lighting unit shown in FIGS. 4, 7 and 8 can also be applied to a direct view capsule endoscope. FIG. 1A is a schematic diagram showing an internal configuration of a direct view capsule endoscope 300. Since the configuration of the direct view capsule endoscope 300 is substantially the same as that of the capsule endoscope 1, the same reference numbers as those of the capsule endoscope 1 are assigned to elements of the direct view capsule endoscope 300 shown in FIG. 11A.

The feature of the direct view capsule endoscope 300 is that light reflected from an object on the front side of the capsule endoscope 300 directly passes through the object lens group 121 to be converged onto the image sensor, and that a plurality of light emitting devices 33 (i.e., six light emitting devices 33 in the example of FIG. 11A) emitting light toward the front side are provided on the positioning plate 301 in place of the lateral light-emission diodes 30a-30f. The light emitting device 33 is, for example, a front light-emission diode.

Figure 11B:
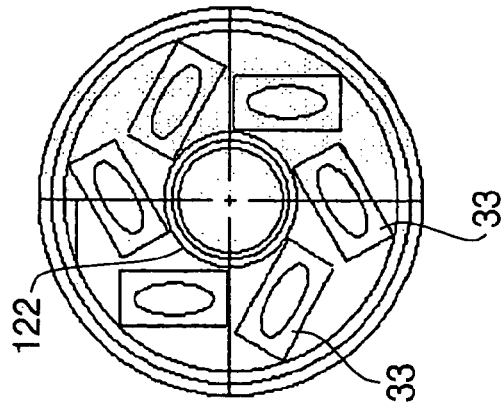
FIG. 11B is a front view of the direct view capsule endoscope shown in FIG. 1A illustrating an arrangement of light emitting devices.

FIG. 11B is a front view of the direct view capsule endoscope 300 illustrating an arrangement of the light emitting devices 33. Similarly to the arrangement shown in FIG. 7, the light emitting devices 33 are arranged like vanes of a windmill around the body tube 122. Each light emitting device 33 is located so that a light emitting surface thereof faces the front side of the capsule endoscope 300.

According to the arrangement of the light emitting devices 33 shown in FIG. 11B, the number of light emitting devices provided in the direct view capsule endoscope can be increased. Therefore, all the image pickup range of the direct view capsule endoscope can be illuminated sufficiently.

When a plurality of types of capsule endoscopes having different performance specifications (e.g., having different sizes or having different light emission wavelengths) are produced, the difference between the arrangements of the light emitting devices can be utilized to specify the type of the capsule endoscope. For example, the capsule endoscope having the arrangement of light emitting devices show in FIG. 4 and the capsule endoscope having the arrangement of light emitting devices shown in FIG. 7 may be configured to emit visible light and infrared light, respectively. Although in the above mentioned embodiment the casing 10 having hermeticity is configured to have a cylindrical shape, the casing 10 may be configured to have another shape, for example, a spherical shape, an elliptical shape or a prismatic shape.

The present disclosure relates to the subject matter contained in Japanese Patent Application No. 2003-309219, filed on Sep. 1, 2003, which is expressly incorporated herein by reference in its entirety.

What is claimed is:

1. A capsule endoscope, comprising:
    a capsule having a substantially cylindrical shape with closed ends, the capsule having a transparent part provided at least at one axial position of the capsule, and the transparent part extending around a circumference of the capsule;
    an omnidirectional objective optical system positioned substantially coaxial with a central axis of the capsule and configured to receive light reflected by objects positioned around the circumference of the capsule through the transparent part, and the omnidirectional objective optical system being configured to focus an image of the objects on a single image plane which is substantially orthogonal to the central axis of the capsule;
    an image pickup device which picks up the image focused by the omnidirectional objective optical system and converts the image into an image signal;
    a plurality of light emitting elements positioned at even angular intervals within the transparent part of the capsule, the plurality of light emitting elements being configured to illuminate substantially all of an image pickup range shot by the omnidirectional objective optical system and the image pickup device, wherein each of the plurality of light emitting elements is positioned so that a central axis of the illuminating light emitted from the plurality of light emitting elements is orthogonal to an optical axis of the omnidirectional objective optical system, and wherein each of the plurality of light emitting elements is positioned so that a central axis of the illuminating light emitted from the plurality of light emitting elements is in a tangential direction of a virtual circle which is coaxial with the omnidirectional objective optical system;
    a transmitter which wirelessly transmits the image signal outputted by the image pickup device; and
    an electric power supply which supplies driving currents to the image pickup device, the plurality of light emitting elements and the transmitter.

2. The capsule endoscope according to claim 1, wherein the plurality of light emitting elements comprises lateral light-emission diodes.

3. The capsule endoscope according to claim 1, wherein the plurality of light emitting elements are positioned so as to avoid interference with object light which passes through the transparent part of the capsule and focuses on the image plane via the omnidirectional objective optical system.

4. The capsule endoscope according to claim 1, wherein the plurality of light emitting elements are positioned on both sides of object light which passes through the transparent part of the capsule and is incident upon the omnidirectional objective optical system to focus on the image plane.

5. The capsule endoscope according to claim 1, wherein the plurality of light emitting elements comprises six light emitting elements positioned at even angular intervals of 60 degrees within the transparent part of the capsule.

6. The capsule endoscope according to claim 1, wherein the omnidirectional objective optical system comprises:
    an object lens group configured to focus the image of the objects on the image plane; and
    a convex reflecting mirror configured to reflect object light entering the capsule through the transparent part so as to guide the object light to the object lens group.

7. The capsule endoscope according to claim 6, wherein the convex reflecting mirror is provided in a shape of a paraboloid of revolution, wherein the convex reflecting mirror is positioned coaxial with an optical axis of the object lens group.

8. A capsule endoscope, comprising:
    a capsule configured to have hermeticity and a transparent part configured to transmit light;
    an objective optical system positioned substantially coaxial with a predetermined axis defined in the capsule, the objective optical system being configured to receive light reflected by objects and to focus an image of the objects on a single image plane which is substantially orthogonal to the predetermined axis of the capsule;
    an image pickup device which picks up the image focused by the objective optical system and converts the image into an image signal;
    a plurality of light emitting elements positioned at even angular intervals within the capsule, the plurality of light emitting elements being configured to illuminate substantially all of an image pickup range shot by the objective optical system and the image pickup device, wherein each of the plurality of light emitting elements is positioned so that a central axis of the illuminating light emitted from the plurality of light emitting elements is orthogonal to an optical axis of the objective optical system, and wherein each of the plurality of light emitting elements is positioned so that a central axis of the illuminating light emitted from the plurality of light emitting elements is in a tangential direction of a virtual circle which is coaxial with the objective optical system;

a transmitter which wirelessly transmits the image signal outputted by the image pickup device; and an electric power supply which supplies driving currents to the image pickup device, the plurality of light emitting elements and the transmitter.

9. A capsule endoscope, comprising:

a capsule configured to have hermeticity and to have a transparent part provided at least at one axial position of a predetermined axis defined in the capsule, the transparent part extending around a circumference of the capsule;

an omnidirectional objective optical system positioned substantially coaxial with the predetermined axis of the capsule, the omnidirectional objective optical system being configured to receive light reflected by objects positioned around the circumference of the capsule through the transparent part, and the onmidirectional objective optical system being configured to focus an image of the objects on a single image plane which is substantially orthogonal to the predetermined axis of the capsule;

an image pickup device which picks up the image focused by the omnidirectional objective optical system and converts the image into an image signal;

a plurality of light emitting elements positioned at even angular intervals within the transparent part of the capsule, the plurality of light emitting element being configured to illuminate substantially all of an image pickup range shot by the omnidirectional objective optical system and the image pickup device, wherein each of the plurality of light emitting elements is positioned so that a central axis of the illuminating light emitted from the plurality of light emitting elements is orthogonal to an optical axis of the omnidirectional objective optical system, and wherein each of the plurality of light emitting elements is positioned so that a central axis of the illuminating light emitted from the plurality of light emitting elements is in a tangential direction of a virtual circle which is coaxial with the omnidirectional objective optical system;

a transmitter which wirelessly transmits the image signal outputted by the image pickup device; and an electric power supply which supplies driving currents to the image pickup device, the plurality of light emitting elements and the transmitter.

10. A capsule endoscope, comprising:

a capsule having a substantially cylindrical shape with closed ends, the capsule having a transparent part provided at least at one axial position of the capsule, and the transparent part extending around a circumference of the capsule;

an omnidirectional objective optical system positioned substantially coaxial with a central axis of the capsule and configured to receive light reflected by objects positioned around the circumference of the capsule through the transparent part, and the omnidirectional objective optical system being configured to focus an image of the objects on a single image plane which is substantially orthogonal to the central axis of the capsule;

an image pickup device which picks up the image focused by the omnidirectional objective optical system and converts the image into an image signal;

a plurality of light emitting elements positioned at even angular intervals within the transparent part of the capsule, the plurality of light emitting elements being configured to illuminate substantially all of an image pickup range shot by the omnidirectional objective optical system and the image pickup device, wherein each of the plurality of light emitting elements is positioned so that a central axis of the illuminating light emitted from the plurality of light emitting elements is orthogonal to an optical axis of the omnidirectional objective optical system, and wherein the plurality of light emitting elements are alternately positioned around an optical axis of the omnidirectional objective optical system at first and second radial position, the first radial position being nearer to the optical axis than second radial positions;

a transmitter which wirelessly transmits the image signal outputted by the image pickup device; and an electric power supply which supplies driving currents to the image pickup device, the plurality of light emitting elements and the transmitter.

11. The capsule endoscope according to claim 10, wherein the plurality of light emitting elements comprises lateral light-emission diodes.

12. The capsule endoscope according to claim 10, wherein the plurality of light emitting elements are positioned so as to avoid interference with object light which passes through the transparent part of the capsule and focuses on the image plane via the omnidirectional objective optical system.

13. The capsule endoscope according to claim 10, wherein the plurality of light emitting elements are positioned on both sides of object light which passes through the transparent part of the capsule and is incident upon the omnidirectional objective optical system to focus on the image plane.

14. The capsule endoscope according to claim 10, wherein the plurality of light emitting elements comprises six light emitting elements positioned at even angular intervals of 60 degrees within the transparent part of the capsule.

15. The capsule endoscope according to claim 10, wherein the omnidirectional objective optical system comprises:

an object lens group configured to focus the image of the objects on the image plane; and a convex reflecting mirror configured to reflect object light entering the capsule through the transparent part so as to guide the object light to the object lens group.

16. The capsule endoscope according to claim 15, wherein the convex reflecting mirror is provided in a shape of a paraboloid of revolution, wherein the convex reflecting mirror is positioned coaxial with an optical axis of the object lens group.

17. A capsule endoscope, comprising:

a capsule configured to have hermeticity and to have a transparent part provided at least at one axial position of a predetermined axis defined in the capsule, the transparent part extending around a circumference of the capsule;

an omnidirectional objective optical system positioned substantially coaxial with the predetermined axis of the capsule, the omnidirectional objective optical system being configured to receive light reflected by objects positioned around the circumference of the capsule through the transparent part, and the omnidirectional objective optical system being configured to focus an image of the objects on a single image plane which is substantially orthogonal to the predetermined axis of the capsule;

an image pickup device which picks up the image focused by the omnidirectional objective optical system and converts the image into an image signal;

a plurality of light emitting elements positioned at even angular intervals within the transparent part of the capsule, the plurality of light emitting element being configured to illuminate substantially all of an image pickup range shot by the omnidirectional objective optical system and the image pickup device, wherein each of the plurality of light emitting elements is positioned so that a central axis of the illuminating light emitted from the plurality of light emitting elements is orthogonal to an optical axis of the omnidirectional objective optical system, wherein the plurality of light emitting elements are alternately positioned around an optical axis of the omnidirectional objective optical system at first and second radial positions, the first radial position being nearer to the optical axis than second radial position;

a transmitter which wirelessly transmits the image signal outputted by the image pickup device; and an electric power supply which supplies driving currents to the image pickup device, the plurality of light emitting elements and the transmitter.

* * * * *